United States Patent [19]

Meilland

[11] Patent Number: Plant 5,396

[45] Date of Patent: Jan. 29, 1985

[54] CLIMBER ROSE PLANT—METZALITAF VARIETY

[75] Inventor: Marie L. Meilland, Antibes, France

[73] Assignee: The Conard-Pyle Company, West Grove, Pa.

[21] Appl. No.: 508,717

[22] Filed: Jun. 28, 1983

[51] Int. Cl.[3] ..... A01H 5/00

[52] U.S. Cl. ..... Plt./2

[58] Field of Search ..... Plt./2

*Primary Examiner*—Robert E. Bagwill

*Attorney, Agent, or Firm*—Burns, Doane, Swecker & Mathis

[57] ABSTRACT

A new and distinct variety of rose plant is provided which bears highly attractive double relatively large blossoms which exhibit a colorful blend of yellow and rouge coloration. The new variety of the present invention resulted from the controlled crossing of an unnamed seed parent obtained by crossing the Meigold variety and the Peer Gynt variety with pollen from an unnamed parent obtained by crossing progeny of a cross between the Meialfi variety and the Meifan variety with the King's Ransom variety. The resulting variety possesses long arching canes as well as glossy deep green foliage. The new variety is particularly suited for growing in the U.S. landscape where climbing or pillar roses are customarily grown.

2 Drawing Figures

SUMMARY OF THE INVENTION

The new and distinct variety of rose plant was originated by me by crossing an unnamed and non-patented variety formed by crossing the Meigold variety (non-patented) and the Peer Gynt variety (non-patented) with pollen from an unnamed and non-patented parent obtained by crossing progeny of a cross between the Meialfi variety (non-patented) and the Meifan variety (non-patented) with the King's Ransom variety (U.S. Plant Pat. No. 2,103). The parentage of the new variety can be summarized as follows: (Meigold×Peer Gynt)×[(Meialfi×Meifan)×King's Ransom].

From this controlled pollination I produced a new and distinct variety of rose plant which when grown in the United States of America as classified in the Climber Class. When grown under the different climatic conditions of Antibes, France the new variety tends to assume the configuration of a Hybrid Tea rose plant. Regardless of where grown the new variety is distinguished from its parents, as well as from all other varieties of which I am aware. This variety was obtained through the selective study of a large number of distinct plants which resulted from the above cross. A single plant resulting from this cross possessed the characteristics of the presently claimed variety.

It was found that the new variety as illustrated herein possesses (a) a vigorous well branched growth habit with long arching canes, (b) buds which open into relatively large extremely attractive blossoms of a richly colored yellow-rouge blend, and (c) attractive leathery and glossy foliage of deep green coloration.

Extensive testing has confirmed the behavior and characteristics of the new variety. The new variety is particularly suited for growing in the landscape where climbing or pillar roses are cutomarily grown.

The characteristics and properties of the new variety are strictly transmissible by asexual propagation, e.g. by budding.

The rose plants of the present variety has been named the Meizalitaf variety. Rose plants of this variety presently are being marketed by the Conard-Pyle Company under the SPECTRA trademark.

BRIEF DESCRIPTION OF THE PHOTOGRAPH

The accompanying photographs show as nearly true as it is possible to make the same in color illustrations of this character, typical specimens of plant parts from two year old plants of the new variety produced from softwood cuttings and growing in the open air at West Grove, Pa., U.S.

In FIG. 1 are shown various plant parts of the new variety during mid-June. At the top of the photograph are illustrated blossoms in various stages of opening with the red or rouge coloration becoming more prominent as the blossoms assume a more fully open configuration. At the right center buds are illustrated. At the left the glossy leaflets of deep green coloration are illustrated, and at the lower right typical banches are illustrated.

In FIG. 2 are illustrated fully mature blossoms during mid-summer wherein substantial red or rouge coloration has become suffused with the yellow coloration. It will be noted that more red or rouge coloration is apparent when the blossoms are subjected to the heat and sunlight of mid-summer. Glossy leaflets are also shown.

DETAILED DESCRIPTION

Figure 1:
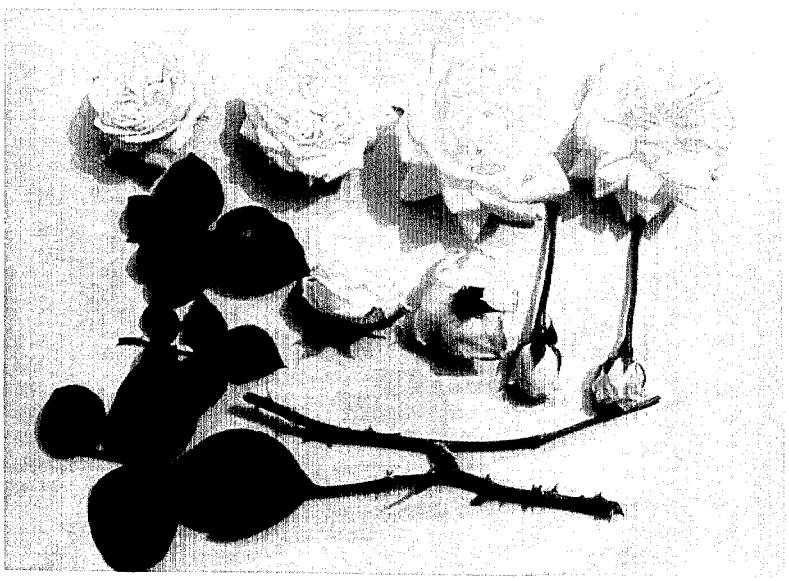
Figure 2:
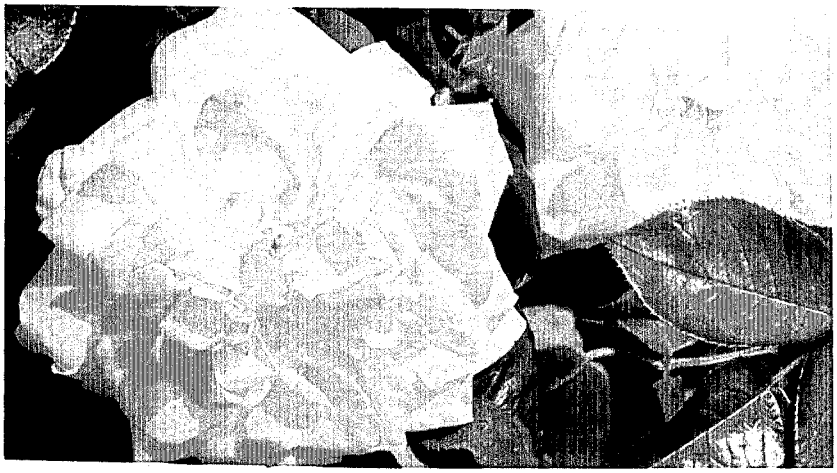

The plants described were grown outside at West Grove, Pa., and were observed during the month of June.

The chart utilized in the identification of the colors is that of The Royal Horticultural Society (R.H.S. Colour Chart).

CLASS

Climber.

PLANT

Habit: Very vigorous, well branched plant, with long arching canes.

BRANCHES

Color:

Young stems.—When the bud on the stem is approximately pea size, Green Group 143C.

*Mature wood.*—After blossom petals drop, Green Group 141B suffused with Red-Purple Group 61B.

Thorns: Few in quantity.

LEAVES

Petioles: The coloration is closest to but darker than Red Group 53A as the foliage matures and there are on the average approximately 2 to 4 small thorns on the underside of the petiole.

Leaflets:

*Number.*—3, 5 (most often) and occasionally 7.

*Shape.*—Ovate in general, with a small portion obovate and eliptic; base is obtuse; apex is acute; margins are serrate.

*Texture.*—Smooth on upperside, rough underneath.

*General appearance.*—Foliage is large and deep green and glossy.

*Color of newly formed foliage.*—Upper surface: Green Group 137B tinged with Red-Purple Group 61B at least to the mid-rib and margin. Under surface: light green diffused with Red-Purple Group 61B.

*Color of adult foliage.*—Upper surface: Yellow-Green Group 147A. Under surface: Yellow-Green Group 147B to 148B.

*Size.*—Widely variable, from approximately 3 to 9 cm. in length, with an average length of approximately 6 cm., and from approximately 2.5 to 6.5 cm. in width, with an average width of approximately 5.0 cm.

INFLORESCENCE

Number of flowers: Usually one flower per stem, however 2 to 3 flowers per stem is not uncommon.

Peduncle From approximately 9.0 to 13.0 cm. in length, with an average length of 10.0 cm., the color at the opening bud stage is substantially identical to that of the petioles and becomes greener as the flower opens.

Bud: Color when first opening: Exterior surface: from very dark red at petal tip (Greyed-Purple Group 187C) to dark red (Greyed-Purple Group 185A) to orange (Orange-Red Group 33B) to greenish-yellow at petal base (Yellow Group 2A). Interior surface: Yellow Group 2A.

Flower:

*Form.*—Fully double with numerous short, irregular petals at the center.

*Diameter.*—Approximately 9.0 to 12.0 cm. for fully open bloom.

*Color during the course of opening.*—Upper surface: Yellow Group 9A with a tinge of Red Group 47C at petal edge. Under surface: Yellow Group 9B.

*Color when fully open.*—Upper surface: Yellow Group 9C with an increased area suffused with Red Group 47C. Under surface: Yellow Group 9C at petal base, fading to 9D at apex.

*Color immediately prior to petal drop.*—Substantially similar to color upon becoming fully open, with the red coloration becoming more prominent.

*Fragrance.*—Slight.

*Lasting quality.*—Long.

DEVELOPMENT

Vegetation Very vigorous.

Blossoming: Abundant in spring, sporadic thereafter.

Hardiness: Moderate.

Resistance to disease: Moderate.

I claim:

1. A new and distinct variety of Climber rose plant, substantially as illustrated and described, characterized particularly by (a) a vigorous well branched growth habit with long arching canes, (b) buds which open into extremely attractive relatively large blossoms of a richly colored yellow-rouge blend, and (c) attractive leathery and glossy foliage of deep green coloration.

* * * * *